United States Patent [19]

Cardenas

[11] Patent Number: 5,616,133
[45] Date of Patent: Apr. 1, 1997

[54] SYRINGE FOR EPIDURAL CATHETER

[76] Inventor: Juan M. Cardenas, 3109 Knob Ct., Owensboro, Ky. 42303

[21] Appl. No.: 547,063

[22] Filed: Oct. 23, 1995

[51] Int. Cl.⁶ ..................................... A61M 5/00
[52] U.S. Cl. ........................... 604/187; 604/236; 604/283
[58] Field of Search ................................. 604/187, 905, 604/246, 247, 283, 256, 167, 236–238; 251/149.1, 149.9; 137/515.7, 511, 515.5

[56] References Cited

U.S. PATENT DOCUMENTS

| | | | |
|---|---|---|---|
| 3,459,177 | 8/1969 | Deuschle | 604/187 X |
| 4,143,853 | 3/1979 | Abramson | 604/246 X |
| 4,150,673 | 4/1979 | Watt . | |
| 4,187,848 | 2/1980 | Taylor | 604/243 |
| 4,464,174 | 8/1984 | Ennis | 604/90 |
| 5,085,643 | 2/1992 | Larkin et al. | 604/152 |
| 5,139,483 | 8/1992 | Ryan | 604/86 |
| 5,251,873 | 10/1993 | Atkinson et al. | 604/905 X |
| 5,284,475 | 2/1994 | Mackal . | |
| 5,322,518 | 6/1994 | Schneider et al. . | |
| 5,334,188 | 8/1994 | Inoue et al. | 604/283 |
| 5,374,248 | 12/1994 | Lopez . | |
| 5,389,086 | 2/1995 | Attermeier et al. . | |
| 5,395,348 | 3/1995 | Ryan | 604/297 |
| 5,520,665 | 5/1996 | Fleetwood | 604/283 |

*Primary Examiner*—Vincent Millin
*Assistant Examiner*—V. Alexander
*Attorney, Agent, or Firm*—Wheat, Camoriano, Smith & Beres, PLC

[57] ABSTRACT

A special epidural catheter syringe, epidural catheter connector, and continuous epidural tubing connector are provided to provide mechanical lockouts to prevent epidural anesthetic from being injected intravenously and to prevent medications intended for intravenous use from being injected into the epidural catheter.

6 Claims, 5 Drawing Sheets

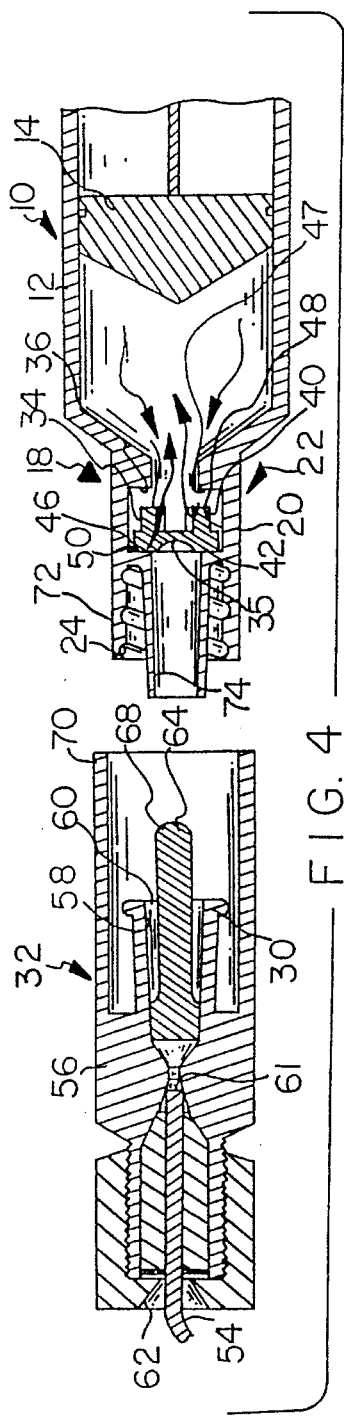
FIG. 4
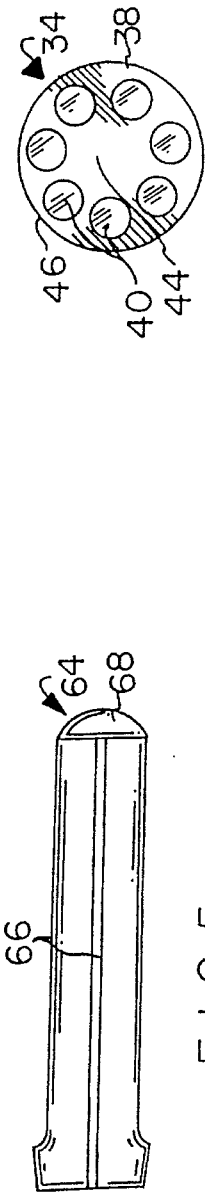
FIG. 5
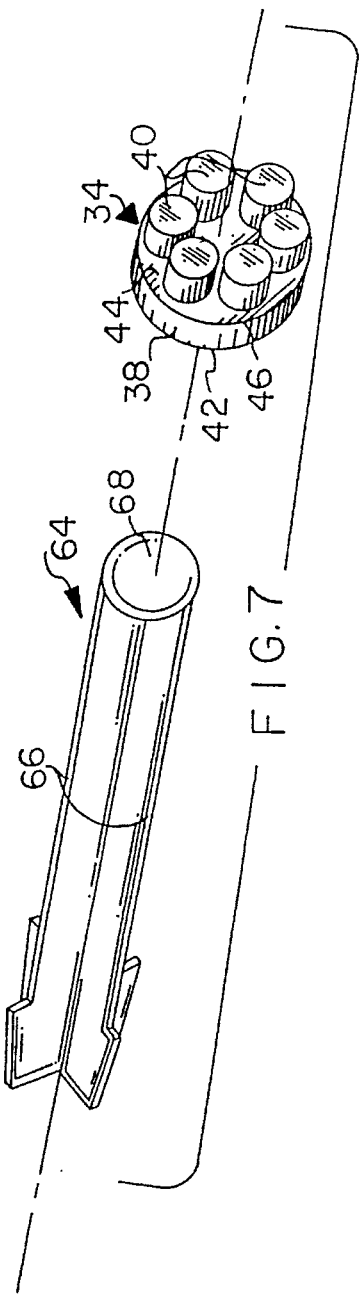
FIG. 6
FIG. 7

SYRINGE FOR EPIDURAL CATHETER

BACKGROUND OF THE INVENTION

Epidural anesthesia is a common form of anesthesia used for lower abdominal, pelvic and lower extremity surgery. It is also used to provide pain relief in certain chronic and acute conditions such as during childbirth.

In general, an epidural anesthetic is administered by inserting an epidural catheter into the epidural space located right outside the spinal cord. A standard epidural catheter connector is then attached to the free end of the epidural catheter. Subsequent to this, a standard syringe containing any of several local anesthetics available, is connected directly to the epidural catheter connector. Gradually, a moderate amount of the local anesthetic is injected so that it passes through the epidural catheter and eventually into the epidural space, flooding any nerves as they come out of the spinal cord.

The degree and level of numbness produced is directly proportional to the amount of local anesthetic injected. In some instances, in addition to the above initial dose, a continuous epidural infusion of either local anesthetics or narcotics or both, is initiated. This continuous infusion can provide pain relief for several days and is accomplished by using an epidural pump, a pump bag containing the medication to be given, and also continuous epidural tubing which connects to the epidural catheter connector.

Prior to receiving an epidural anesthetic, all patients have an intravenous line started in order to administer fluids and other medications. This intravenous line has either injection ports along the way or stopcocks or both, through which medications can be given. Injection into an intravenous line port is achieved by using a standard syringe with a needle attached to it. Injection into a stopcock is accomplished by using a standard syringe without a needle.

In summary, standard syringes are now being used to inject medications both into an epidural catheter and into an intravenous line present in the same patient concurrently. If the large quantity of local anesthetic that is intended to be injected into the epidural catheter is accidentally injected into the intravenous line, severe neurologic and cardiovascular problems, up to and including death, can occur.

Alternatively, if some medications that are intended for intravenous use are accidentally injected into the epidural space, the patient may suffer severe temporary or permanent damage depending on the nature of the drug injected.

Anesthesiologists and nurse anesthetists are extremely careful in labelling and using these standard syringes to try to minimize the occurrence of such erroneous injections. However, anesthesiologists and nurse anesthetists are also human, and, despite the most careful precautions, these accidental injections continue to occur.

SUMMARY OF THE INVENTION

The purpose of the present invention is to provide a mechanical device which greatly reduces the opportunity for the human errors described above.

The present invention provides a special epidural catheter syringe which can only inject into a special epidural catheter connector. Since this special syringe cannot inject into an intravenous line or elsewhere, the anesthesiologist or nurse anesthetist cannot accidentally inject the large quantity of local anesthetic from the special epidural catheter syringe into the wrong place.

The special epidural catheter syringe of the present invention includes a check valve, which allows liquid to enter the syringe but prevents liquid from leaving the syringe unless the syringe is connected to a special epidural catheter connector, which opens the check valve and allows liquid to flow out of the syringe.

The present invention also provides a special epidural catheter connector for use with the special epidural catheter syringe. This epidural catheter connector cannot receive medication from a standard syringe, so anesthetic in a standard syringe intended for an intravenous line cannot accidentally be injected into this epidural catheter connector.

The present invention also provides a special continuous epidural tubing connector, which allows continuous infusions to be made into the special epidural catheter connector and which prevents these infusions from being given intravenously.

Thus, the present invention provides mechanical devices to help avoid accidentally injecting epidural anesthetic intravenously and to help avoid accidentally injecting medication intended for a vein into the epidural catheter.

BRIEF DESCRIPTION OF THE DRAWINGS

FIG. 4 is the same view as FIG. 3, but with the connector and syringe separated from each other;

FIG. 5 is a side view of the pusher portion of the connector of FIG. 3;

FIG. 6 is an end view of the valve member of the syringe of FIG. 1;

FIG. 7 is an exploded perspective view showing the pusher and valve member of FIG. 3;

DESCRIPTION OF THE PREFERRED EMBODIMENT

Figure 1:
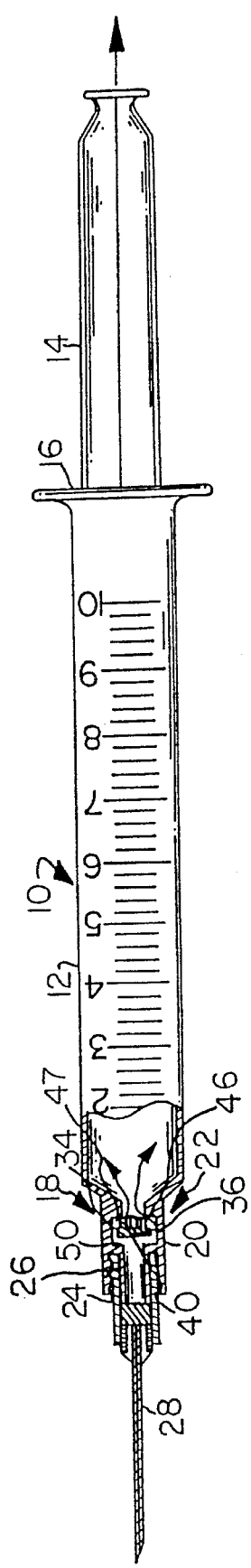
FIG. 1 is a side view partially in section of a preferred embodiment of the epidural catheter syringe of the present invention, showing the plunger being pulled out of the syringe.

As shown in FIGS. 1–4, the special epidural catheter syringe 10 includes a hollow cylinder portion 12, with a plunger 14 in the hollow cylinder 12 and projecting out a first end 16 of the cylinder 12.

Figure 2:
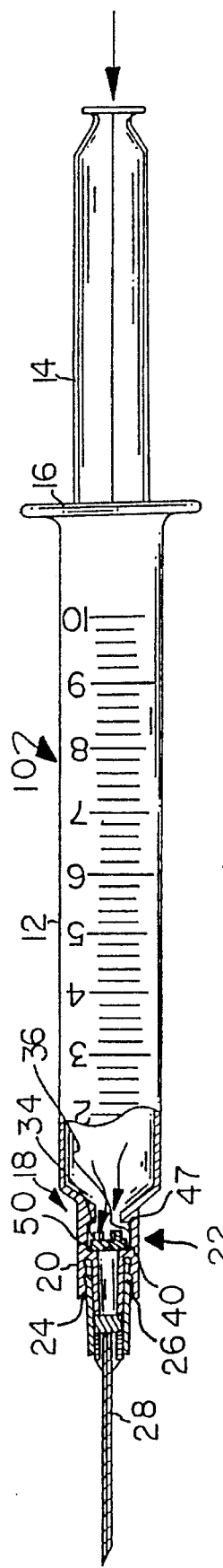
FIG. 2 is the same view as FIG. 1, but with the plunger being pushed into the syringe.
Figure 3:
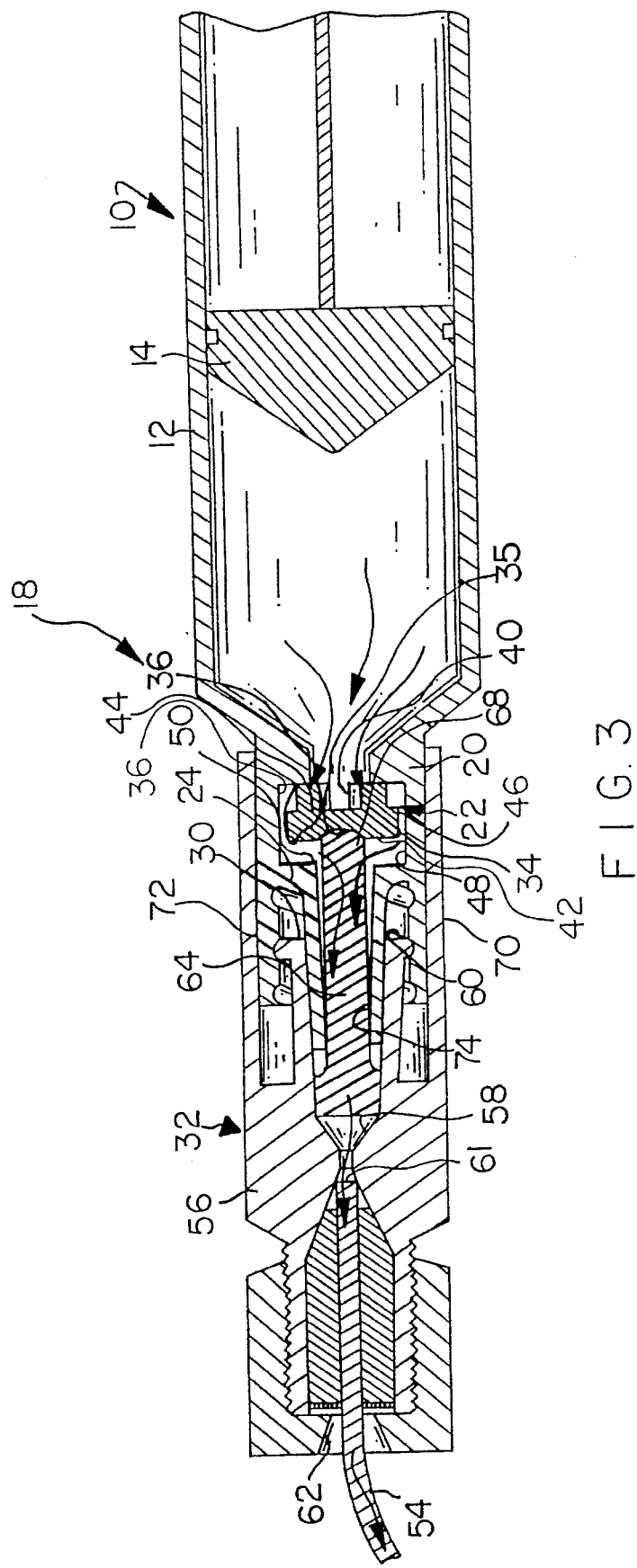
FIG. 3 is the same view as FIG. 2, but with the syringe broken away and with a special epidural catheter connector connected to the syringe, both the connector and the end of the syringe being shown in section.

The second end 18 of the cylinder 12 includes a reduced diameter portion 20, in which is located a check valve 22. Beyond the check valve 22 is a female luer lock portion 24, which can mate with the male luer lock portion 26 of a standard needle 28 as shown in FIG. 2 or with the male luer lock portion 30 of a special epidural catheter connector 32, as shown in FIG. 3. Luer locks are similar to a threaded connection and are well known in the art.

The check valve 22 is made up of a movable valve member 34, which is located in a valve chamber 36 in the reduced diameter portion 20 of the syringe 10. The movable valve member 34 can be seen in more detail in FIGS. 6 and 7. The movable valve member 34 is a disc 38 having two faces 42, 44, with legs 40 projecting out of one face 44 of the disc near the outer edge 46 of the disc 38. The other face 42 of the disc 38 is substantially flat, except that it has a central, circular indentation 35, which cooperates with the connector 32 as will be described later.

As shown in FIG. 1, when the plunger 14 is pulled out of the syringe 10 to draw in liquid, the movable valve member 34 moves to the right until the legs 40 of the valve member 34 abut the first end wall 47 of the valve chamber 36. In this position, liquid can flow into the second end 18 of the syringe 10, between the outer edge 46 of the valve member 34 and the cylindrical wall 48 of the valve chamber 36, then between the legs 40 of the valve member 34 and into the hollow cylinder 12 of the syringe 10. This position of the plunger 14 and valve 34 is used for filling the syringe 10 with the local anesthetic that is used in an epidural anesthetic procedure.

As shown in FIG. 2, if the physician or nurse anesthetist attempts to inject the local anesthetic from the syringe 10 by pushing the plunger 14 into the cylinder 12, the pressure of the liquid in the syringe 10 pushes the movable valve member 34 to the left, where it seals against the wall 50 of the valve chamber 36, preventing any liquid from escaping out the second end 18 of the syringe 10. In tests of a prototype of the embodiment described herein, it has been shown that, if the syringe 10 is turned to a vertical position, with the needle 28 pointing upwardly, and if the plunger is pushed in slowly, the check valve 22 will permit gas to escape out the second end of the syringe 10. However, as soon as liquid reaches the movable valve member 34, it moves to the closed position, preventing the liquid from leaving the syringe 10.

Since the check valve 22 prevents liquid from leaving the syringe 10, the syringe 10 cannot be used to inject directly into a patient's vein or into an intravenous line. In fact, the only way liquid can leave the special epidural catheter syringe 10 is by connecting the syringe 10 to a special epidural catheter connector 32, as shown in FIGS. 3 and 4.

Looking first at FIG. 4, the epidural catheter connector 32 is shown connected to an epidural catheter 54. The epidural catheter connector 32 is made up of a body 56 which defines a fluid pathway 58 from the syringe end opening 60 of the connector 32 to the catheter end opening 62 of the connector 32. A pusher member or projection 64, made up of vanes 66 (shown in FIGS. 5 and 7) and having a circular end 68, extends from the body 56 of the connector 32 and projects through the syringe end opening 60 of the fluid path 58. There is a male luer lock portion 30 adjacent the syringe opening 60, as was mentioned earlier. There is also a sleeve 70 which surrounds the male luer lock portion 30, leaving a gap between the sleeve 70 and the luer lock portion 30. The sleeve 70 extends beyond the pusher 64.

The catheter end of the connector 32 connects to the free end 61 of the catheter 54. There are several different types of epidural catheter connectors known in the art, and the catheter end of the connector 32 may be made in accordance with any known design. The catheter end 62 of the connector 32 simply clamps onto and seals around the catheter 54 so that fluid can be pushed through the catheter 54 from the syringe end of the connector.

In order to connect the epidural catheter connector 32 to the epidural catheter syringe 10, as shown in FIG. 3, the syringe end 60 of the connector 32 is brought into alignment with the end of the syringe 10. The sleeve 70 helps guide the two pieces into proper alignment by sliding over the outside surface 72 of the end of the syringe 10. As the two parts are brought together, the male luer lock portion 30 of the connector 32 meets the internal threads of the female luer lock portion 24 of the syringe 10, and the two parts are threaded together snugly, to form a seal between the syringe 10 and the connector 32. Also, as the two parts are being brought together, the end 68 of the pusher 64 of the connector 32 contacts the central indentation 35 of the movable valve member 34 of the syringe 10, pushing the valve member 34 away from the wall 50, thereby opening a fluid path from the hollow cylindrical portion 12 of the syringe 10 into the fluid pathway 58 of the connector 32.

It should be noted that the inside diameter 74 of the tip of the syringe 10 is larger than the inside diameter of the end of a standard syringe, in order to permit the pusher 64 to enter and reach the valve member 34. This is accomplished by making the wall thickness of the tip of the syringe 10 less than in a standard syringe. In this manner, the luer lock portion 24 of the syringe 10 remains a standard size, while the inside diameter of the opening is enlarged. It should also be noted that the face 42 of the movable valve member 34 has a circular indentation 35, which receives the circular end 68 of the pusher 64.

When the epidural catheter connector 32 is coupled with the epidural catheter syringe 10, as shown in FIG. 3, the mating luer locks 24, 30 provide a seal between the syringe 10 and the connector 32, so that, when the plunger 14 is pushed into the syringe 10, the pressurized liquid in the syringe 10 passes around the valve member 34, out the end of the syringe 10, along the vanes 66 of the pusher 64, and into the fluid pathway 58 into the end 61 of the epidural catheter 54, then through the catheter 54 to the epidural space of the patient (not shown), where it floods the tissue in that space.

Now, referring to FIGS. 8–11, it can be seen that standard syringes or needles cannot be used to inject fluid through the special epidural catheter connector 32 into the catheter 54 and to the epidural space (not shown). In order for liquid to be injected through the connector 32, there must be a seal between the device providing the pressurized fluid and the connector 32, so that fluid can be pushed through the catheter 54 to the epidural space. If there is not a good seal, the fluid will leak out to the atmosphere rather than being pushed through the catheter 54. In none of FIGS. 8–11 can such a seal be made.

Figure 8:
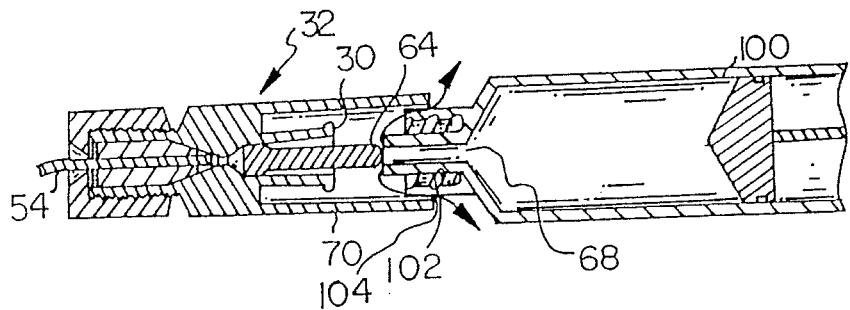
FIG. 8 is a side sectional view showing a standard syringe with a luer lock end unsuccessfully trying to inject into the epidural catheter connector of FIG. 3.

FIG. 8 shows a standard syringe 100 with a luer lock end 102 attempting to inject into the epidural catheter connector 32. As was mentioned earlier, the inside diameter of the tip of a standard syringe 100 is smaller than the inside diameter of the syringe of the present invention, so that the pusher 64 of the epidural catheter connector 32 will not go up inside the end of the standard syringe 100. Instead, the end 68 or the pusher 64, being solid, closes off the opening of the end of the standard syringe 100 and prevents the syringe 100 from injecting and from going up inside the sleeve 70 to mate with the male luer lock portion 30 of the connector to make a seal.

If any liquid makes it out of the syringe 100 and past the pusher 64, it will simply leak out through the gap 104 between the syringe 100 and the connector 32. Since there is no seal between the syringe 100 and the connector 32, fluid under pressure cannot be forced through the connector 32 and catheter 54 to reach the patient.

Figure 9:
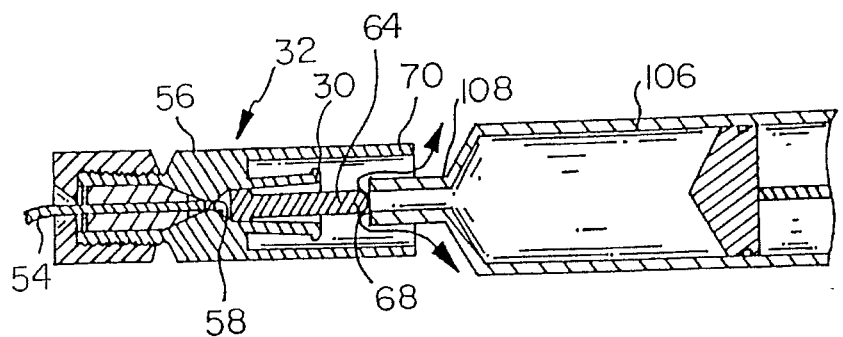
FIG. 9 is a side sectional view showing a standard syringe with a slip tip unsuccessfully trying to inject into the epidural catheter connector of FIG. 3.

Similarly, referring to FIG. 9, if a standard syringe 106 with a slip tip 108 attempted to inject directly into the connector 32, the pusher 64 would interfere with the end of the syringe 106 and again would tend to close it off. Even if the pusher 64 does not seal off the end of the syringe 106, there is still no way to make a seal between the syringe 106 and the connector 32 in order to permit liquid under pressure to be pushed through the connector 32 and catheter 54 to the patient.

Figure 10:
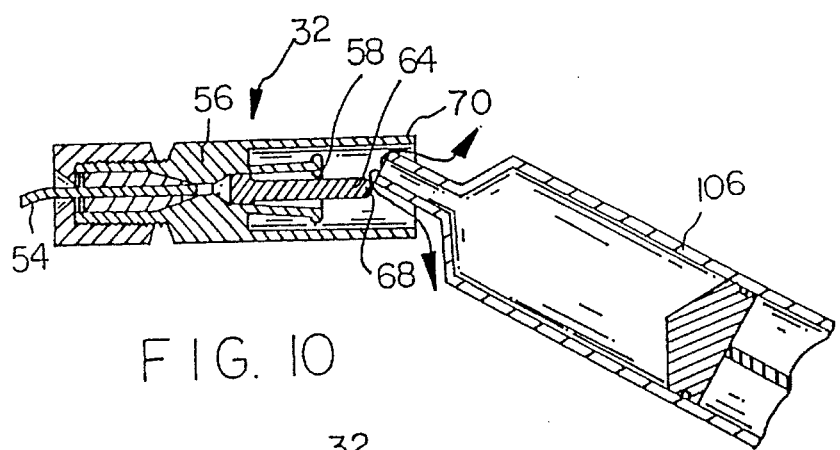
FIG. 10 is a side sectional view showing another unsuccessful attempt to inject from a standard syringe with a slip tip into the epidural catheter connector of FIG. 3.

Referring to FIG. 10, if the standard syringe 106 approached at an angle, it still could not make a seal with the connector 32, so the liquid would still leak out rather than being forced through the catheter 54.

Figure 11:
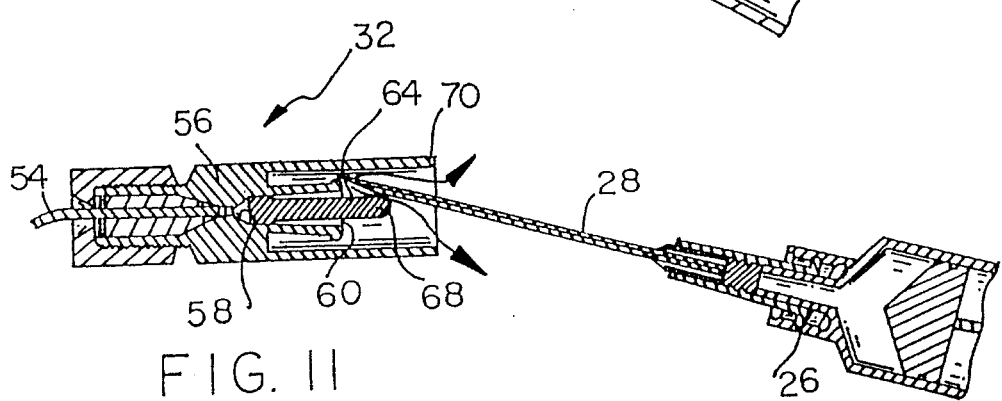
FIG. 11 is a side sectional view showing a standard syringe with a needle unsuccessfully attempting to inject into the epidural catheter connector of FIG. 3.

Referring to FIG. 11, if a needle were used to try to inject into the connector 32, again there is no way to make a seal between the needle and the connector 32. Again, the liquid would leak out from between the needle and the connector 32 instead of passing through the connector and the catheter 54 to the patient.

So, it is clear that only the special epidural catheter syringe 10 can be used to inject into this epidural catheter connector 32.

Figure 12:
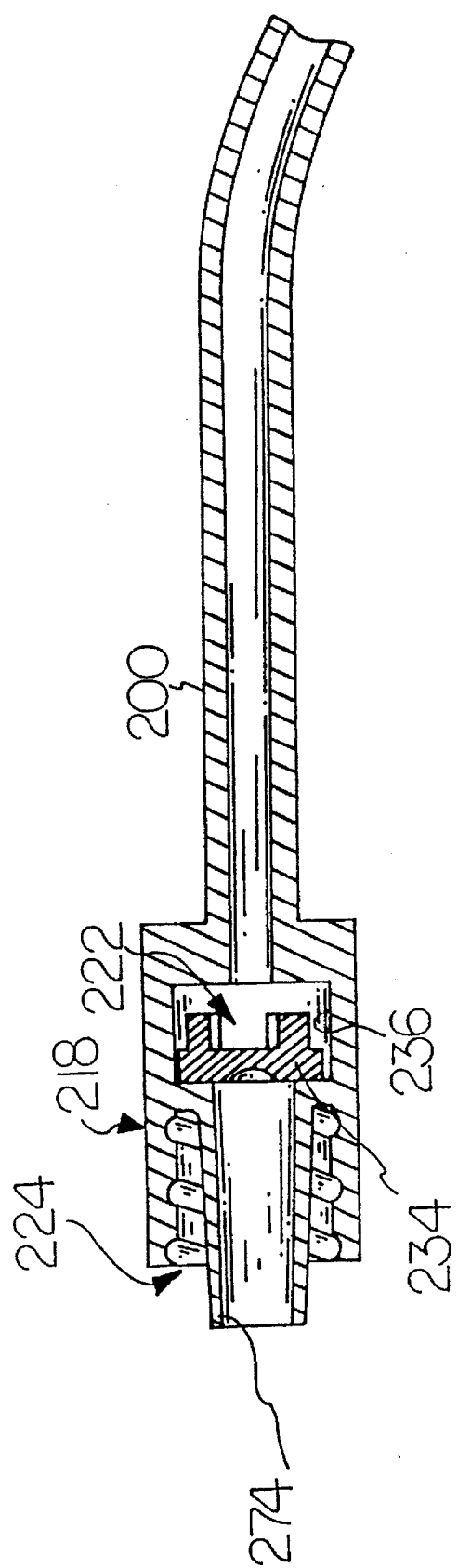
FIG. 12 is a side sectional view of a special continuous epidural tubing connector to be used for giving continuous infusions into the epidural catheter connector.

FIG. 12 shows some standard infusion tubing 200, which would be connected to an infusion bag (not shown) for continuous infusions into the epidural catheter. The end of the tubing 200 includes a device 218, which is essentially the same as the device 18 at the end of the syringe 10 of FIGS. 1–3. The device 218 is intended to allow the infusion tubing to be connected to the special epidural catheter connector 32 of FIG. 3. The device 218 includes a check valve 222, made up of a valve chamber 236, with a movable valve member 234 in the valve chamber 236. At the free end of the device 218 is a female luer lock portion 224. A tip projects out from the device 218 and has a larger inside diameter 274 than does a standard syringe.

The device 218 may be referred to herein as a continuous epidural infusion tubing connector, since it permits the tubing for continuous infusion to be connected to the epidural catheter connector and prevents the medication which is in the tubing from accidentally being infused intravenously. The epidural infusion tubing connector 218 is connected to the epidural catheter connector 32 in the same manner as is the syringe 10, as shown in FIG. 3.

Thus, the present invention has provided mechanical devices which help the anesthesiologist and nurse anesthetist prevent the occurrence of human error, both by preventing the improper injection of medications intended for intravenous use into an epidural catheter and by preventing the improper injection of the epidural anesthetic into a vein.

It will be obvious to those skilled in the art that modifications may be made to the embodiment described above without departing from the scope of the present invention.

What is claimed is:

1. A syringe, comprising:

a hollow cylinder having first and second ends;

a plunger in said hollow cylinder, said plunger extending out of said first end and being movable outwardly and inwardly relative to the cylinder;

a check valve in fluid communication with the second end of said cylinder, wherein said check valve permits liquid to enter the second end of the cylinder when the plunger is pulled outwardly but prevents liquid from leaving the cylinder when the plunger is pushed inwardly.

2. A syringe as recited in claim 1, wherein said hollow cylinder has a reduced diameter portion at its second end, said check valve being located in said reduced diameter portion.

3. A syringe as recited in claim 2, wherein said syringe includes a female luer lock portion for receiving a needle at the end of said reduced diameter portion beyond the check valve.

4. A syringe and catheter connector combination, comprising:

a syringe, comprising:
      a hollow cylinder having first and second ends;
      a plunger in said hollow cylinder, said plunger extending out of said first end and being movable outwardly and inwardly relative to the cylinder;
      a check valve in fluid communication with the second end of said cylinder, wherein said check valve permits liquid to enter the second end of the cylinder when the plunger is pulled outwardly but prevents liquid from leaving the cylinder when the plunger is pushed inwardly; and a catheter connector, comprising:
      a body defining a fluid pathway having a syringe end opening and a catheter end opening; and
      including a projection extending through said syringe end opening, such that said projection pushes said check valve open when said catheter connector is connected to said syringe, so as to permit liquid to flow out the second end of said syringe and through said fluid pathway.

5. A syringe and catheter connector combination as recited in claim 4, and further comprising:

a first luer lock portion on the second end of said hollow cylinder of said syringe;

a second luer lock portion on the syringe end of said catheter connector which mates with the first luer lock portion of the syringe, and wherein said projection extends beyond said second luer lock portion of said connector.

6. A syringe and catheter connector combination as recited in claim 5, wherein said syringe has a reduced diameter end, and the syringe end of said catheter connector also includes an outer sleeve which fits over the reduced diameter end of said syringe to help guide the syringe and connector together for assembly.

* * * * *